United States Patent
Zheng et al.

(10) Patent No.: US 10,352,873 B2
(45) Date of Patent: Jul. 16, 2019

(54) INDUSTRIAL VISUAL STETHOSCOPE SYSTEM AND INDUSTRIAL VISUAL STETHOSCOPE METHOD

(71) Applicant: Nanjing Yuanjue Information and Technology Company, Nanjing (CN)

(72) Inventors: Liming Zheng, Nanjing (CN); Zheng Zhang, Nanjing (CN); Tao Yu, Nanjing (CN)

(73) Assignee: Nanjing Yuanjue Information and Technology Company, Nanjing (CN)

( * ) Notice: Subject to any disclaimer, the term of this patent is extended or adjusted under 35 U.S.C. 154(b) by 0 days.

(21) Appl. No.: 15/800,086

(22) Filed: Nov. 1, 2017

(65) Prior Publication Data

US 2018/0335392 A1 Nov. 22, 2018

(30) Foreign Application Priority Data

May 18, 2017 (CN) .......................... 2017 1 0350319

(51) Int. Cl.
| | |
|---|---|
| *G01N 21/88* | (2006.01) |
| *G01N 21/954* | (2006.01) |
| *G01N 21/41* | (2006.01) |
| *G01B 11/16* | (2006.01) |
| *G01N 21/952* | (2006.01) |
| *G01C 15/00* | (2006.01) |

(52) U.S. Cl.
CPC ......... *G01N 21/8851* (2013.01); *G01B 11/16* (2013.01); *G01N 21/41* (2013.01); *G01N 21/8806* (2013.01); *G01N 21/952* (2013.01); *G01N 21/954* (2013.01); *G01C 15/002* (2013.01)

(58) Field of Classification Search
CPC ........ G01N 21/41; G01N 21/55; G01N 21/64; G01N 21/94; G01N 21/954; G01N 21/958; G01N 21/8851; G01N 2201/105; G01N 2201/0683; G01N 2201/06113; G01B 11/16; G01C 15/002
See application file for complete search history.

(56) References Cited

U.S. PATENT DOCUMENTS

| | | | |
|---|---|---|---|
| 2014/0226866 A1* | 8/2014 | Crandall | G01N 21/274 382/107 |
| 2017/0336330 A1* | 11/2017 | Meeks | G01N 21/958 |

* cited by examiner

*Primary Examiner* — Jamil Ahmed
(74) *Attorney, Agent, or Firm* — Anna Tsang

(57) ABSTRACT

An industrial visual stethoscope system and a detecting method are provided. The system has a base, a workpiece support, a single-color lighting device, a camera module, a rotating device, and an analyzing device. When the single-color light irradiates the workpiece, if the single-color light irradiates into the crack which is relatively deep and narrow, the single-color light is rarely to be reflected out of the crack. But if the single-color light irradiates into the scar, the single-color light is reflected out of the scar due to the specular reflection. During the relative rotation, when the reflected light enters the camera module in parallel, the energy of the light is concentrated, causing overexposure and forming obvious white light. Thus, the analyzing device can identify the recess is a scar formed by hit rather than a crack formed by heat.

10 Claims, 20 Drawing Sheets

INDUSTRIAL VISUAL STETHOSCOPE SYSTEM AND INDUSTRIAL VISUAL STETHOSCOPE METHOD

BACKGROUND OF THE INVENTION

1. Field of the Invention

The present invention relates to an industrial visual stethoscope system and an industrial visual stethoscope method, especially to an industrial visual stethoscope system and a method for distinguishing cracks caused by forging from scars caused by exterior impact.

2. Description of the Prior Arts

Nowadays, many appliances or components are made from cylindrical metal workpiece by various kinds of processing, such as forging, casting or turning. The workpiece may get heated due to high speed abrasion or other reason during the process, or the workpiece may even be directly under heat treatment. When the workpiece is cooled down, crystallites inside of the metal workpiece may be rearranged. With reference to FIG. 15, as this time, a crack A may be formed on an outer surface of the workpiece. The crack A may cause a great impact on a structural strength of the workpiece, and thus any workpiece will be under detection to find out the defective product having the crack A.

With reference to FIG. 16, however, the workpiece may get hit and then form scars B during the manufacturing or in transportation. The scars B may not affect the structural strength of the workpiece, and are ignorable. But it is hard to distinguishing the cracks A from the scars B with the naked eyes, and thus a specific detecting method is needed.

The most common detecting method is using fluorescent powder. When the workpiece is magnetized, the workpiece is covered by fluorescent powder and then rinsed with water to remove the fluorescent powder. The crack is relatively deep and narrow, while the scar is relatively shallow and wide, such that the fluorescent powder inside the cracks is hard to be washed away. Then, the workpiece is irradiated with a fluorescent lamp, and if there are recesses shining with fluorescent light, these recesses are cracks.

However, the aforementioned detecting method by using fluorescent powder has the following shortcomings. First, the fluorescent powder pollutes and damages the environment, and is also harmful to the human body. Second, the crack may be formed in an inner wall of the workpiece if the workpiece is a tube, and the conventional fluorescent detecting method is not applied to detect the inner wall of the tube.

To overcome the shortcomings, the present invention provides an industrial visual stethoscope system and an industrial visual stethoscope method to mitigate or obviate the aforementioned problems.

SUMMARY OF THE INVENTION

The main objective of the present invention is to provide an industrial visual stethoscope system and an industrial visual stethoscope method that are environmentally friendly and safe to the human body, and is applicable for detecting an inner wall of a tube.

The industrial visual stethoscope system has a base, a workpiece support, at least one single-color lighting device, at least one camera module, a rotating device, and an analyzing device. The workpiece support is mounted on the base for accommodating a workpiece to be detected. The at least one single-color lighting device is mounted on the base, and is disposed toward the workpiece support. The at least one camera module is mounted on the base, and is disposed toward the workpiece support. The rotating device is mounted on the base to relatively rotate the workpiece on the workpiece support and a group comprising the at least one single-color lighting device and the at least one camera module. The analyzing device is electrically connected to the at least one camera module for analyzing a film filmed by the at least one camera module to distinguish a recess that is overexposed in the film due to specular reflection on the workpiece.

The industrial visual stethoscope method has the following steps:

(a) preparing materials, wherein a workpiece, a single-color lighting device, and a camera module are prepared; and the single-color lighting device and the camera module are disposed toward the workpiece;

(b) filming, wherein the workpiece and a group comprising the single-color lighting device and the camera module are relatively rotated; wherein simultaneously, the single-color lighting device irradiates the workpiece with a single-color light, and the camera module films the workpiece;

(c) distinguishing, wherein an analyzing device distinguishes a recess that is overexposed due to specular reflection on the workpiece by a film filmed by the camera module and then the analyzing device records the result; afterwards, comparing all the recesses on the workpiece with the recess that is exposed in the film; if there is any recess that is not overexposed, said recess not overexposed is a crack.

When the single-color light irradiates the workpiece, if the single-color light irradiates into the crack which is relatively deep and narrow, the single-color light is rarely to be reflected out of the crack. But if the single-color light irradiates into the scar, which is relatively shallow and wide, the single-color light is reflected out of the scar due to the specular reflection. During the relative rotation, when the reflected light enters the camera module in parallel, the energy of the light is concentrated since the light enters at the right angle, thereby causing overexposure and forming obvious white light. Thus, the analyzing device can identify the recess is a scar formed by hit rather than a crack formed by heat.

The present invention detects whether a large area of specular reflection is incurred via the alternation of an incident angle to make the reflected light enter the camera module in parallel to form overexposure when the camera module is forming images, thereby the analyzing device can distinguish the scar from the crack.

The present invention detects the scar and the crack only via the single-color lighting device and the camera module, such that the present invention will not harm the environment and human body, which is different from the conventional detecting method using fluorescent powder with chemical solvent that may pollute the environment.

In addition, the single-color lighting device and the camera module may be mounted through a tubular workpiece, thereby detecting an inner wall of the tubular workpiece. Furthermore, compared with the conventional detecting method using fluorescent powder, the present invention can be implemented automatically, thereby reducing the manpower cost and increasing the detecting efficiency.

Other objectives, advantages and novel features of the invention will become more apparent from the following detailed description when taken in conjunction with the accompanying drawings.

DETAILED DESCRIPTION OF THE PREFERRED EMBODIMENTS

Figure 1:
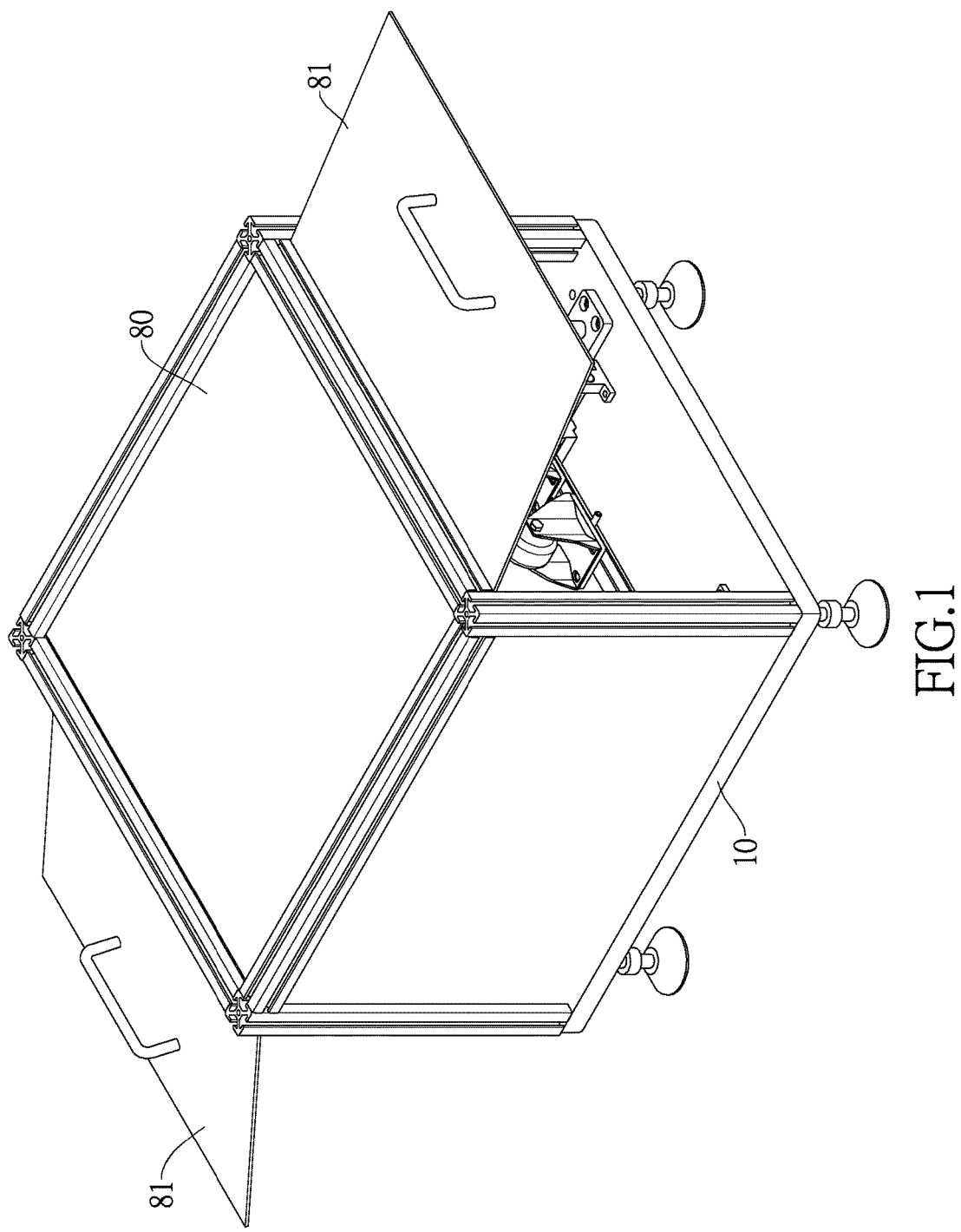
FIG. 1 is a perspective view of a first embodiment of an industrial visual stethoscope system in accordance with the present invention.
Figure 2:
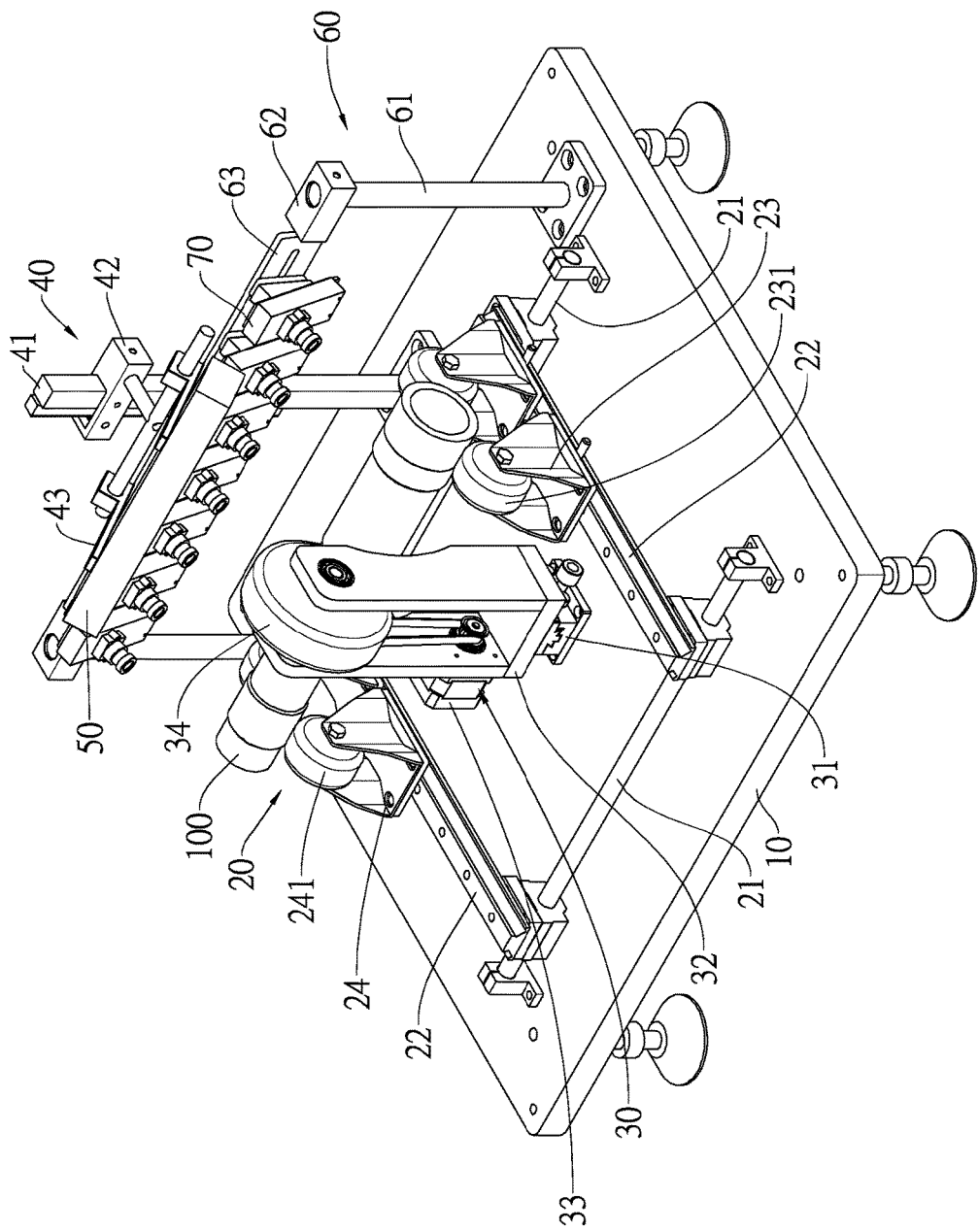
FIG. 2 is an exploded perspective view of the industrial visual stethoscope system in FIG. 1.
Figure 3:
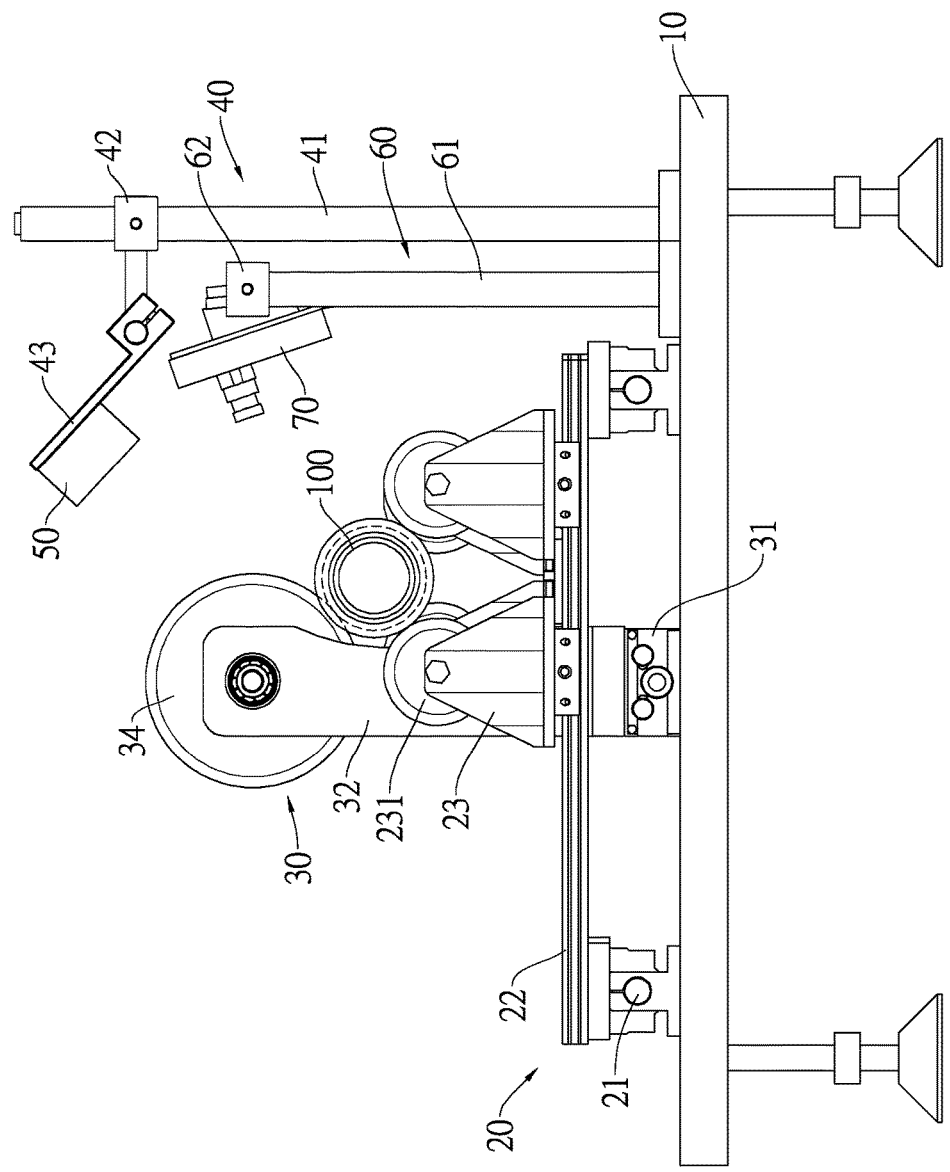
FIGS. 3 and 4 are side views of the industrial visual stethoscope system in FIG. 1, showing fitting workpieces of different sizes.
Figure 4:
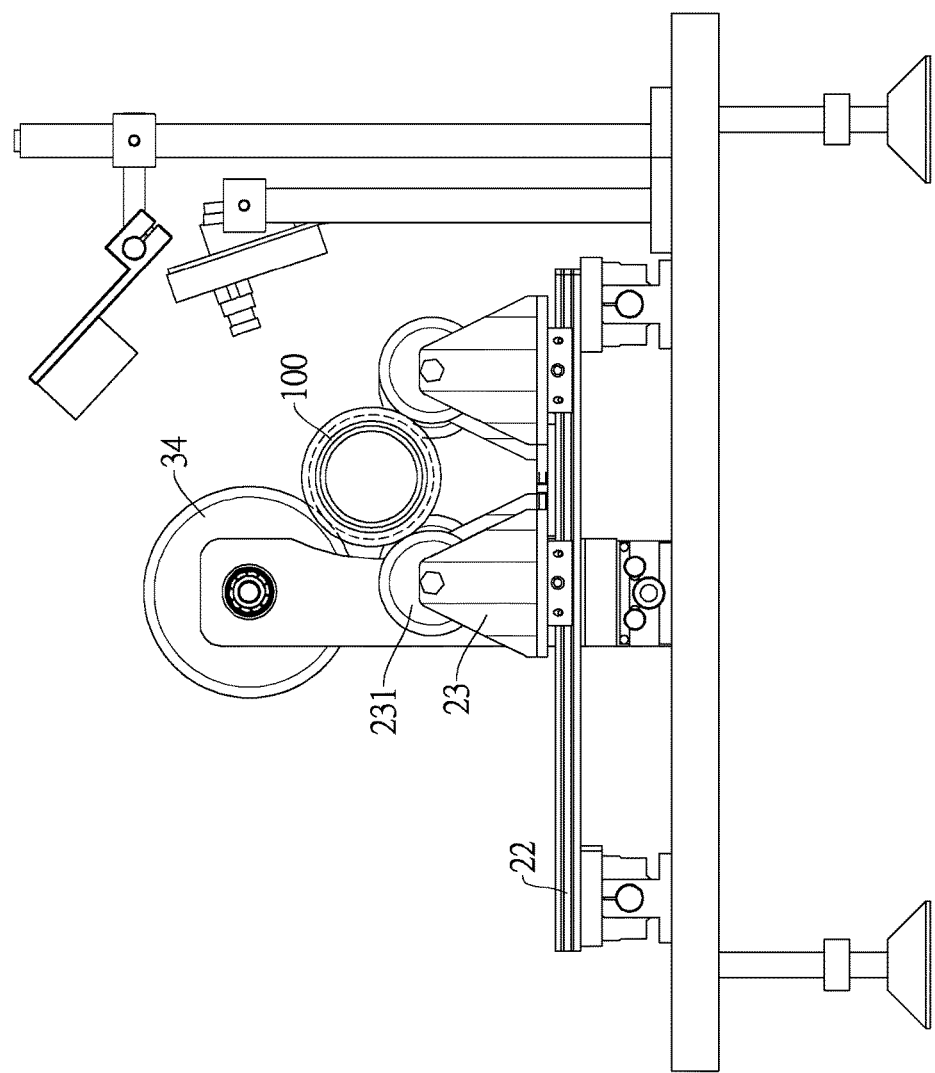
Figure 5:
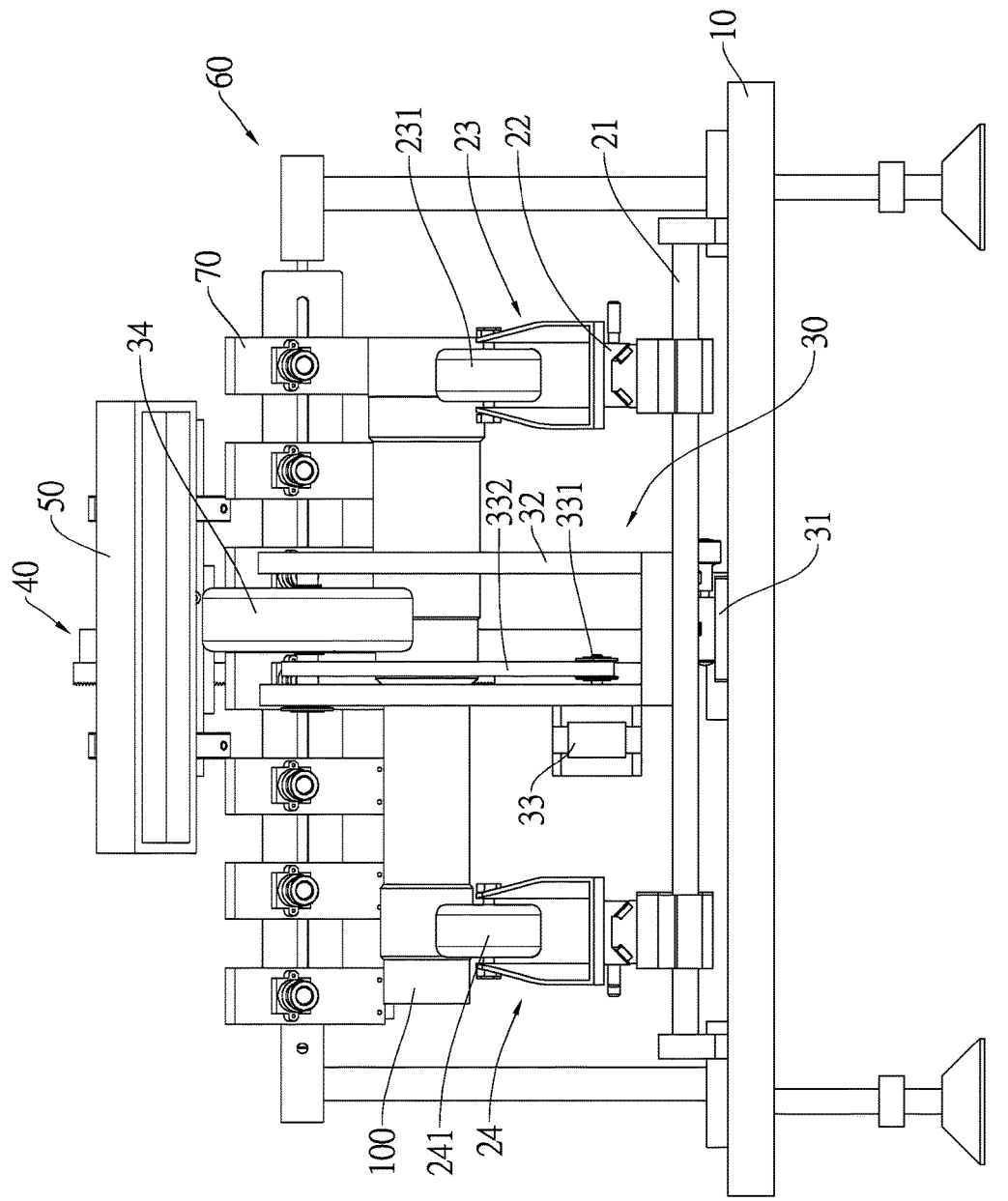
FIG. 5 is a front view of the industrial visual stethoscope system in FIG. 1.
Figure 6:
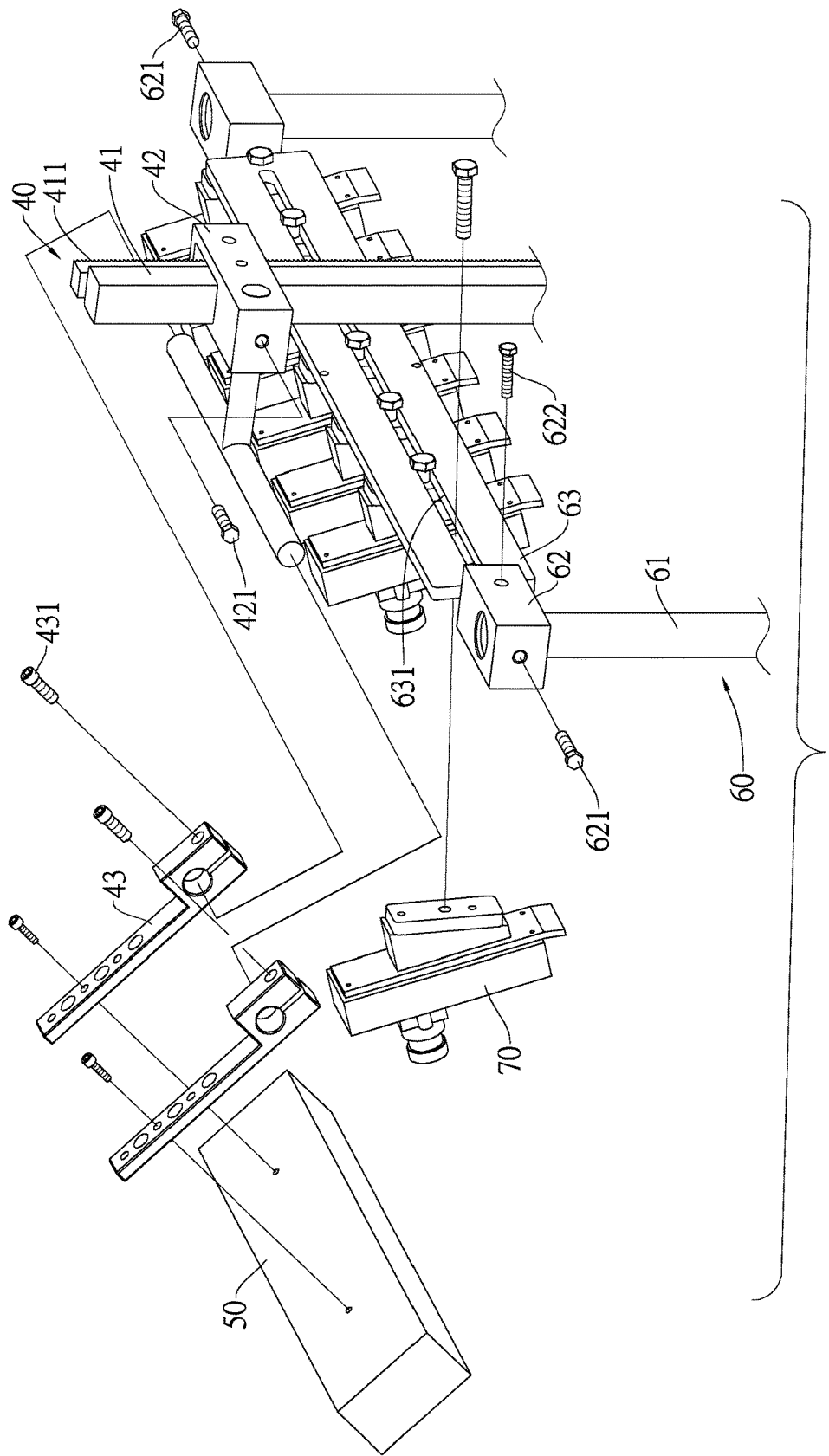
FIG. 6 is a perspective view of a lighting frame and a camera frame of the industrial visual stethoscope system in FIG. 1.

With reference to FIGS. 1 and 2, a first embodiment of an industrial visual stethoscope system in accordance with the present invention comprises a base 10, a workpiece support 20, a rotating device 30, a lighting frame 40, a single-color lighting device 50, a camera frame 60, multiple camera modules 70, a cover 80, and an analyzing device.

In a preferred embodiment, the base 10 is preferably, but not limited to, a panel platform. But the base 10 also can be in any other shape.

With reference to FIGS. 2 to 5, the workpiece support 20 is mounted on the base 10, and is for accommodating a workpiece to be detected. In a preferred embodiment, the workpiece support 20 has two base channels 21, two wheel seat channels 22, two first wheel seats 23, and two second wheel seats 24.

The two base channels 21 are spaced apart from each other. In a preferred embodiment, the base channel 21 is preferably, but not limited to, an elongated round rod.

The wheel seat channels 22 are perpendicular to the base channels 21 in extending directions. Each of the wheel seat channels 22 is movably mounted across the two base channels 21. In a preferred embodiment, the wheel seat channel 22 is preferably, but not limited to, a trapezoid in shape, and two ends of a bottom of the wheel seat channel 22 are respectively mounted around the two base channels 21.

The two first wheel seats 23 are movably mounted on one of the wheel seat channels 22, and the two second wheel seats 24 are movably mounted on the other wheel seat channel 22. Therefore, the first wheel seats 23 and the second wheel seats 24 are spaced apart from each other, and horizontal positions of the two first wheel seats 23 and two second wheel seats 24 may be adjusted via the base channels 21 and the wheel seat channels 22.

In a preferred embodiment, each of the first wheel seats 23 and the second wheel seats 24 is mounted with a screw. When the screw is rotated to tightly abut the wheel seat channel 22, the first wheel seats 23 and the second wheel seats 24 are fixed relative to the wheel seat channels 22. When the screw is loosened, the first wheel seats 23 and the second wheel seats 24 are movable relative to the wheel seat channels 22. Consequently, a distance between the two first wheel seats 23 and a distance between the two second wheel seats 24 may be adjusted to fit workpieces 100 of different sizes. In addition, since the distance between the two first wheel seats 23 can be different from the distance between the two second wheel seats 24, the first wheel seats 23 and the second wheel seats 24 can fit a workpiece 100 having different diameters in different axial positions. However, the structures of the first wheel seats 23 and the second wheel seats 24 are not limited by the aforementioned, and may be altered depending on demand.

Each of the first wheel seats 23 has a rotating wheel 231, and the two rotating wheels 231 of the two first wheel seats 23 respectively abut two sides of the workpiece 100. Each of the second wheel seats 24 has a rotating wheel 241, and the two rotating wheels 241 of the two second wheel seats 24 respectively abut two sides of the workpiece 100. The workpiece 100 is put on the rotating wheels 231, 241, and the rotating wheels 231, 241 can effectively lower the abrasion to avoid damage to the workpiece 100. The structure of the workpiece support 20 is not limited by the aforementioned, and may be altered depending on demand.

The rotating device 30 is mounted on the base 10, and is for providing a relative rotation between the workpiece 100 on the workpiece support 20 and a group comprising the single-color lighting device 50 and the camera module 70. In a preferred embodiment, the rotating device 30 is for rotating the workpiece 100 on the workpiece support 20. But in another preferred embodiment, the rotating device 30 may be for rotating the group that comprises the single-color lighting device 50 and the camera module 70.

In a preferred embodiment, the rotating device 30 has a sliding seat 31, a main frame 32, a motor 33, and an abutting wheel 34. The sliding seat 31 is mounted on the base 10. The main frame 32 is movably mounted on the sliding seat 31, and the main frame 32 also can be fixed on the sliding seat 31. To be specific, the sliding seat 31 is mounted with a screw. When the screw is rotated to tightly abut a bottom of the main frame 32, the main frame 32 is fixed relative to the sliding seat 31. When the screw is loosened, the main frame 32 is movable relative to the sliding seat 31. The motor 33 and the abutting wheel 34 are mounted on the main frame 32. The motor 33 drives the abutting wheel 34 via a pulley 331 and a belt 332. The abutting wheel 34 is for abutting and rotating the workpiece 100 on the workpiece support 20. Since the rotating device 30 is movable relative to the base 10, the abutting wheel 34 can abut workpieces of different sizes. In addition, the rotating device 30 may be altered to make the abutting wheel 34 up-and-down movable relative to the base 10, which also can fit workpieces of different sizes. The structure of the rotating device 30 is not limited by the aforementioned, and may be altered depending on demand.

Figure 19:
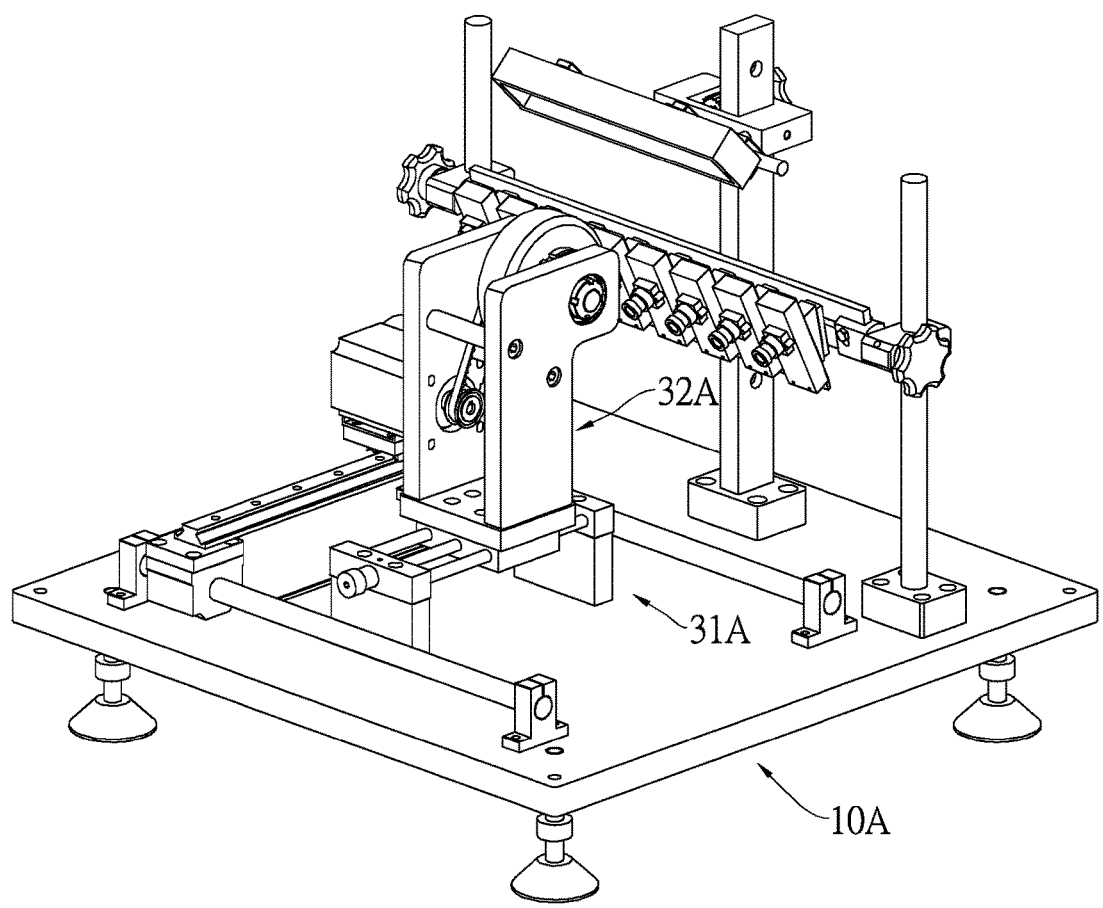
FIG. 19 is a perspective view of another embodiment of an industrial visual stethoscope system in accordance with the present invention.

With reference to FIG. 19, in another preferred embodiment, the sliding seat 31A may be lengthened, thereby increasing the adjusted distance of the main frame 32 relative to the base 10A.

Figure 7:
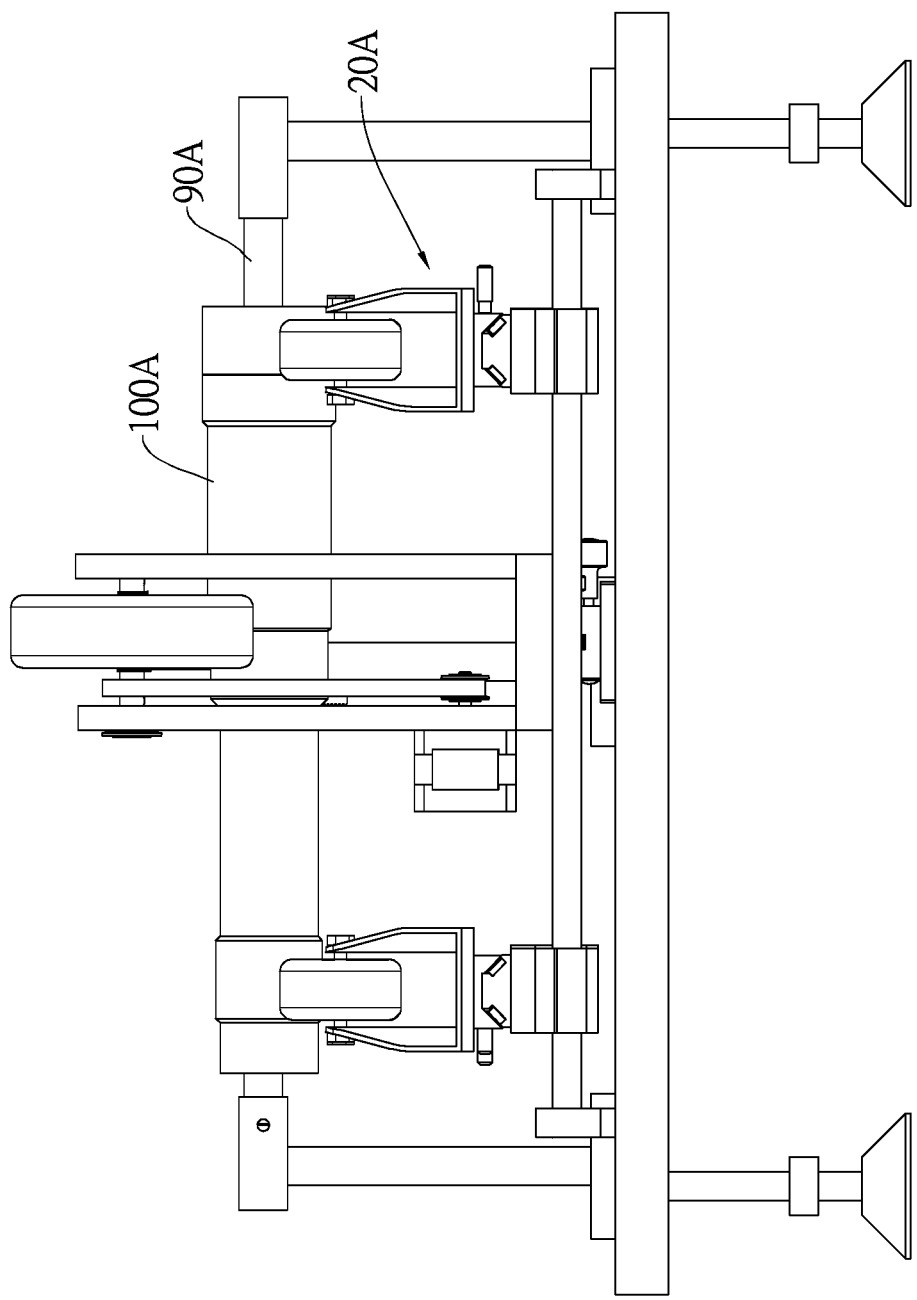
FIG. 7 is a front view of a second embodiment of an industrial visual stethoscope system in accordance with the present invention.
Figure 8:
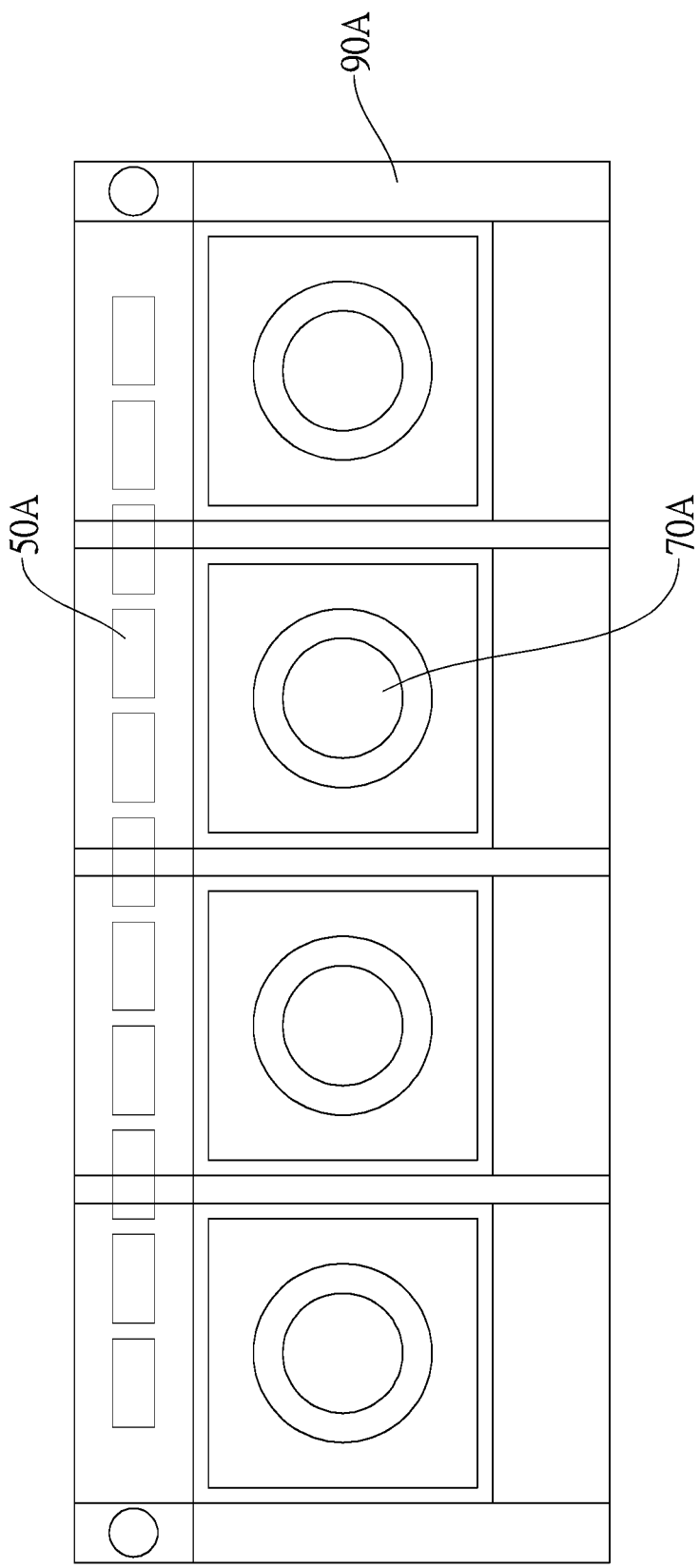
FIG. 8 is a front view of an inside frame, a single-color lighting device, and a camera frame of the industrial visual stethoscope system in FIG. 7.
Figure 9:
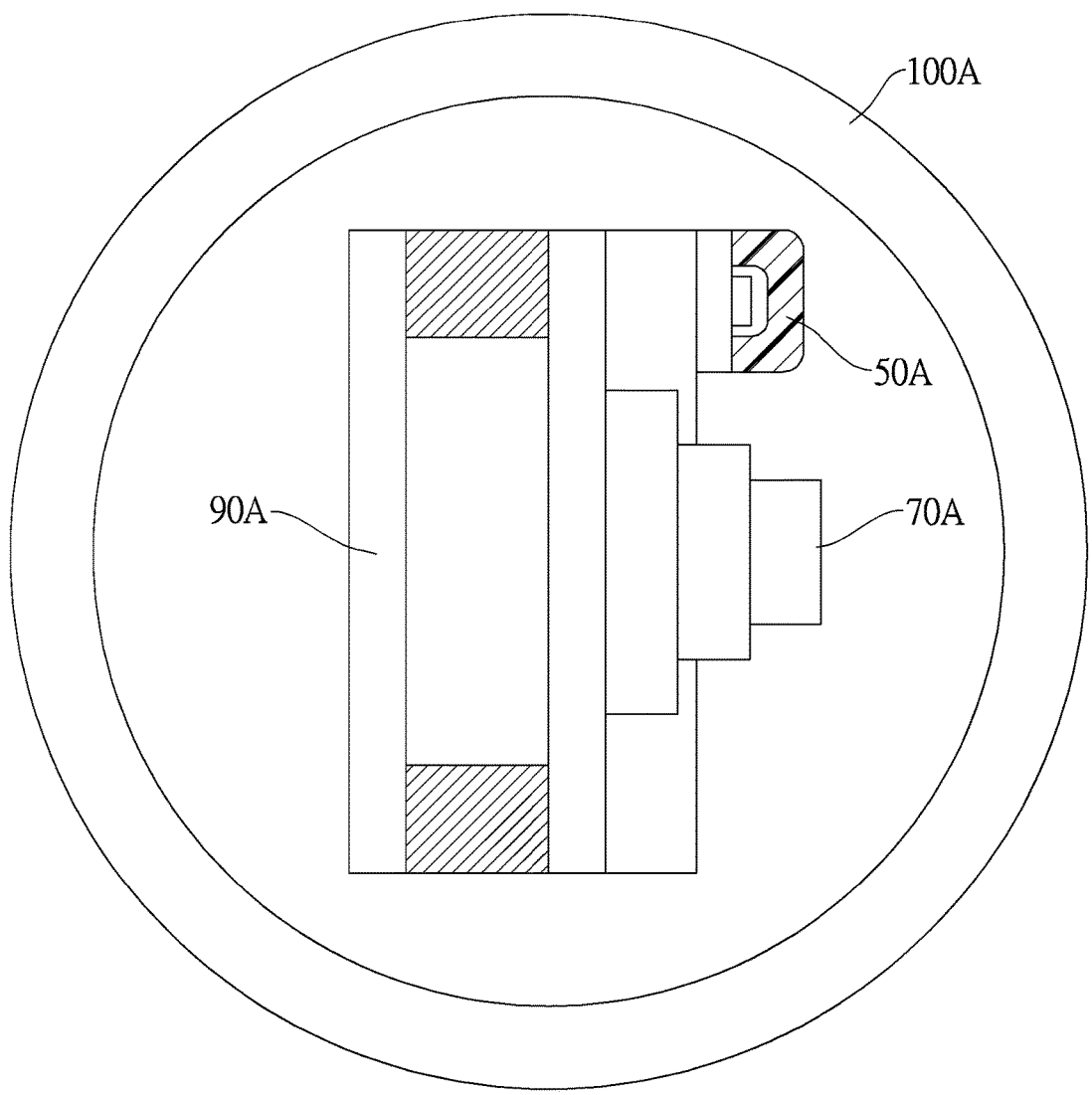
FIG. 9 is a side view of the inside frame, the single-color lighting device, and the camera frame of the industrial visual stethoscope system in FIG. 7.

In addition, the aforementioned rotating device 30 rotates the workpiece 100 by abutting a transverse outer wall of the workpiece 100, and the rotating wheels 231, 241 of the wheel seats 23, 24 also support the workpiece 100 by abutting the transverse outer wall of the workpiece 100. As such, the workpiece support 20 and the rotating device 30 do not contact two axial ends of the workpiece 100, and thus the two ends of the workpiece 100 can be used in other situations. For example, in the following second embodiment, an inside frame 90A protrudes through the workpiece 100A from its two axial ends as shown in FIGS. 7 to 9.

With reference to FIGS. 2, 3, 5, and 6, the lighting frame 40 is mounted on the base 10. The single-color lighting device 50 is mounted on the lighting frame 40, and is up-and-down movable and up-and-down tiltable relative to the lighting frame 40. The single-color lighting device 50 is disposed toward the workpiece support 20.

In a preferred embodiment, the lighting frame 40 has an erect rod 41, an elevatable seat 42, and two mounting seats 43. The erect rod 41 is mounted on the base 10. The elevatable seat 42 is up-and-down movably mounted around the erect rod 41. The elevatable seat 42 is mounted with a screw 421 tightly abutting the erect rod 41 to selectively fix a relative position between the elevatable seat 42 and the erect rod 41. In addition, the erect rod 41 is mounted with a gear rack 411 to engage the elevatable seat 42, thereby precisely adjusting the relative position between the elevatable seat 42 and the erect rod 41. The two mounting seats 43 are up-and-down tiltably mounted around the elevatable seat 42. Each of the mounting seats 43 is mounted with a screw 431 tightly abutting the elevatable seat 42 to selectively fix the relative angle between the mounting seat 43 and the elevatable seat 42. Thus, the single-color lighting device 50 on the mounting seat 43 is up-and-down movable and up-and-down tiltable. The structure of the lighting frame 40 is not limited by the aforementioned. The present invention may be implemented without the lighting frame 40, and the single-color lighting device 50 is directly mounted on the base 10.

In a preferred embodiment, the single-color lighting device 50 emits light in the red color, which has a relatively long wavelength and is highly photo-sensitive. But light of the single-color lighting device 50 also can be altered to any other color depending on demand.

In a preferred embodiment, the present invention includes only one single-color lighting device 50, but the amount of the single-color lighting device 50 also can be multiple depending on demand.

The camera frame 60 is mounted on the base 10, and the camera module 70 is mounted on the camera frame 60. The camera module 70 is up-and-down movably and up-and-down tiltable relative to the camera frame 60. The camera module 70 is disposed toward the workpiece support 20. In a preferred embodiment, the present invention comprises multiple camera modules 70, and the camera modules 70 are linearly aligned on the camera frame 60, thereby fitting an elongated workpiece 100. But the amount and the arrangement of the camera module 70 are not limited by the aforementioned, and may be altered according to the size and shape of the workpiece 100. For example, the present invention can be implemented with only one camera module 70.

In a preferred embodiment, the camera frame 60 has two feet 61, two connecting seats 62, and a transverse frame 63. The feet 61 are mounted on the base 10 and are spaced apart from each other. The two connecting seats 62 are up-and-down movably mounted around the two feet 61 respectively. Each of the connecting seats 62 is mounted with a screw 621 tightly abutting the feet 61 to selectively fix a relative position between the connecting seat 62 and the feet 61. Two ends of the transverse frame 63 are respectively mounted in the two connecting seats 62. One of the two connecting seats 62 is mounted with a screw 622 tightly abutting an end of the transverse frame 63 to selectively fix a relative angle between the transverse frame 63 and the feet 61. Thus, the camera module 70 on the transverse frame 63 is up-and-down movable and up-and-down tiltable.

In addition, the camera module 70 is transversely moveably mounted on the camera frame 60. To be specific, the transverse frame 63 is formed with an elongated hole 631. The camera module 70 is fixed on the elongated hole 631 through a screw, and thus a transverse position of the camera module 70 relative to the camera frame 60 is adjustable. The structure of the camera frame 60 is not limited by the aforementioned. The present invention may be implemented without the camera frame 60, and the camera module 70 is directly mounted on the base 10.

In a preferred embodiment, the camera module 70 is preferably, but not limited to, a Charge-coupled Device (CCD) or a Complementary Metal-Oxide Semiconductor (CMOS).

With reference to FIGS. 1 and 2, the cover 80 is mounted on the base 10, and enclosing the workpiece support 20, the rotating device 30, the lighting frame 40, the single-color lighting device 50, the camera frame 60, and the camera module 70. An inner wall of the cover 80 is an unreflecting black wall, thereby providing a fine environment for filming. In a preferred embodiment, the cover 80 has two doors 81 respectively on two opposite sides of the cover 80.

In addition, outer surfaces of all the components inside the cover 80 may be black to further avoid light reflection to provide a fine environment for filming.

Figure 20:
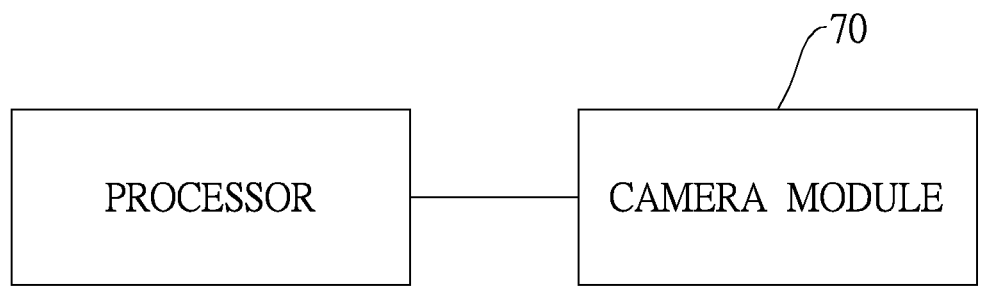
FIG. 20 is a functional block diagram showing an analyzing device and the camera module in accordance with the present invention.

The analyzing device is electrically connected to the camera module 70 as shown in FIG. 20 for analyzing a film from the camera module 70 to distinguish a recess that is overexposed in the film due to specular reflection on the workpiece 100. The analyzing device then compares all the recesses on the workpiece 100 with the recess that is overexposed in the film. If there is any recess that is not overexposed, said recess not overexposed is a crack.

The aforementioned first embodiment of the industrial visual stethoscope system is for detecting an outer surface of the workpiece 100. With reference to FIGS. 7 to 9, a second embodiment of the industrial visual stethoscope system in accordance with the present invention is for detecting an inner wall of a tubular workpiece 100A. The second embodiment of the industrial visual stethoscope system is substantially similar to the first embodiment. But in the second embodiment, the single-color lighting device 50A and the camera module 70A are mounted on an inside frame 90A. The inside frame 90A is disposed above the workpiece support 20A, and is mounted through the tubular workpiece 100A. The second embodiment has multiple single-color lighting devices 50A and multiple camera modules 70A, which respectively are linearly aligned on the inside frame 90A, thereby detecting the inner wall of the tubular workpiece 100A.

In addition, in a preferred embodiment, the inside frame 90A is an integrated elongated panel. But the inside frame 90A also can comprise two parts respectively mounted in the tubular workpiece 100A from two ends of the tubular workpiece 100A, and then the two parts are connected to each other.

Figure 10:
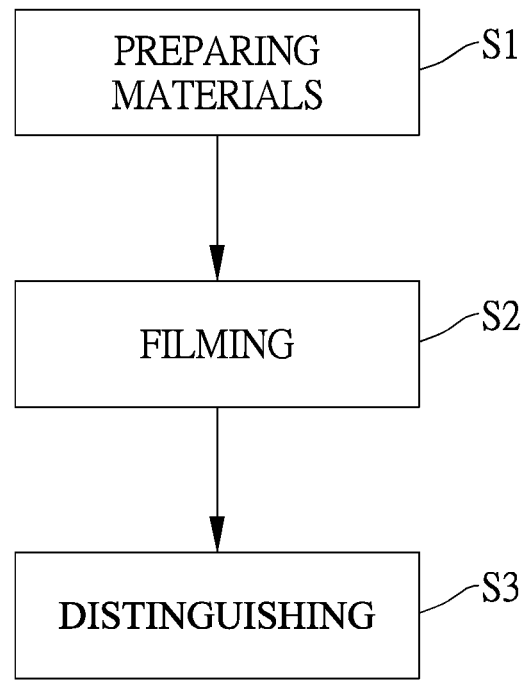
FIG. 10 is a flow chart of an industrial visual stethoscope method in accordance with the present invention.
Figure 11:
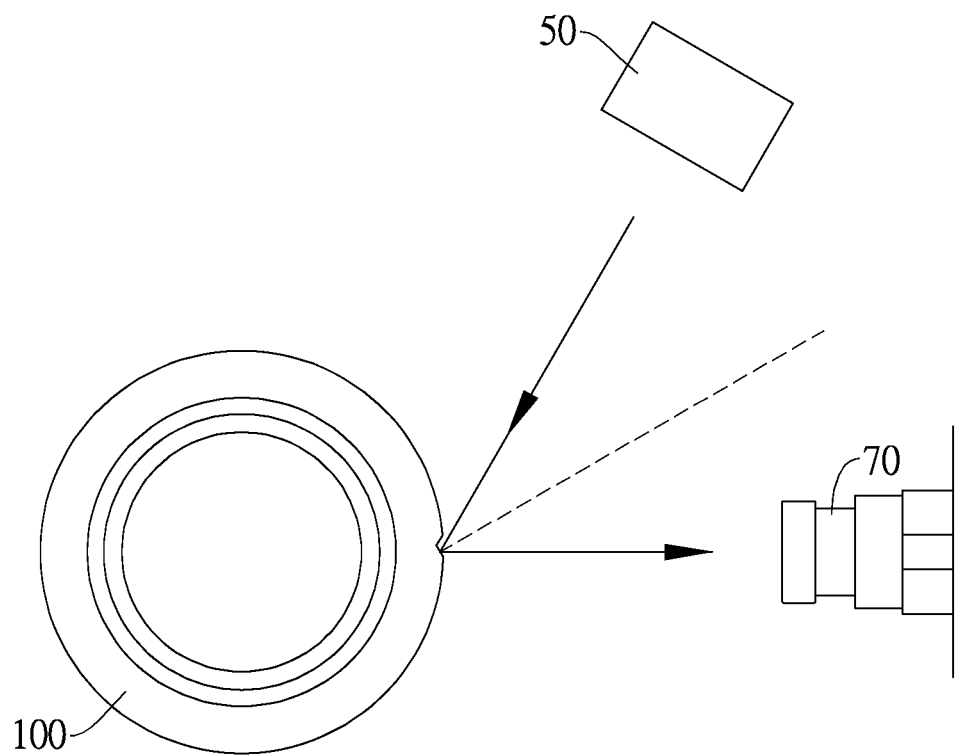
FIG. 11 is a schematic view of the specular reflection of the industrial visual stethoscope method in FIG. 10.

With reference to FIG. 10, an industrial visual stethoscope method in accordance with the present invention comprises the following steps.

The first step (S1) is to prepare materials. A workpiece 100, a single-color lighting device 50, and a camera module 70 are prepared, and the single-color lighting device 50 and the camera module 70 are disposed toward the workpiece 100.

In the first step, the material can be any one of the two aforementioned embodiments of the industrial visual stethoscope system. It is not limited thereto, as long as the material includes the single-color lighting device 50 and the camera module 70, and the workpiece 100 and a group comprising the single-color lighting device 50 and the camera module 70 are rotatable relative to each other.

In addition, in the first step, the shape of the workpiece 100 is not limited, and may be any shape other than the aforementioned tubular shape. The workpiece 100 may be hollow or solid.

The second step (S2) is to film. The workpiece 100 and the group comprising the single-color lighting device 50 and the camera module 70 are relatively rotated. Simultaneously, the single-color lighting device 50 irradiates the workpiece 100 with a single-color light, and the camera module 70 films the workpiece 100.

Figure 12:
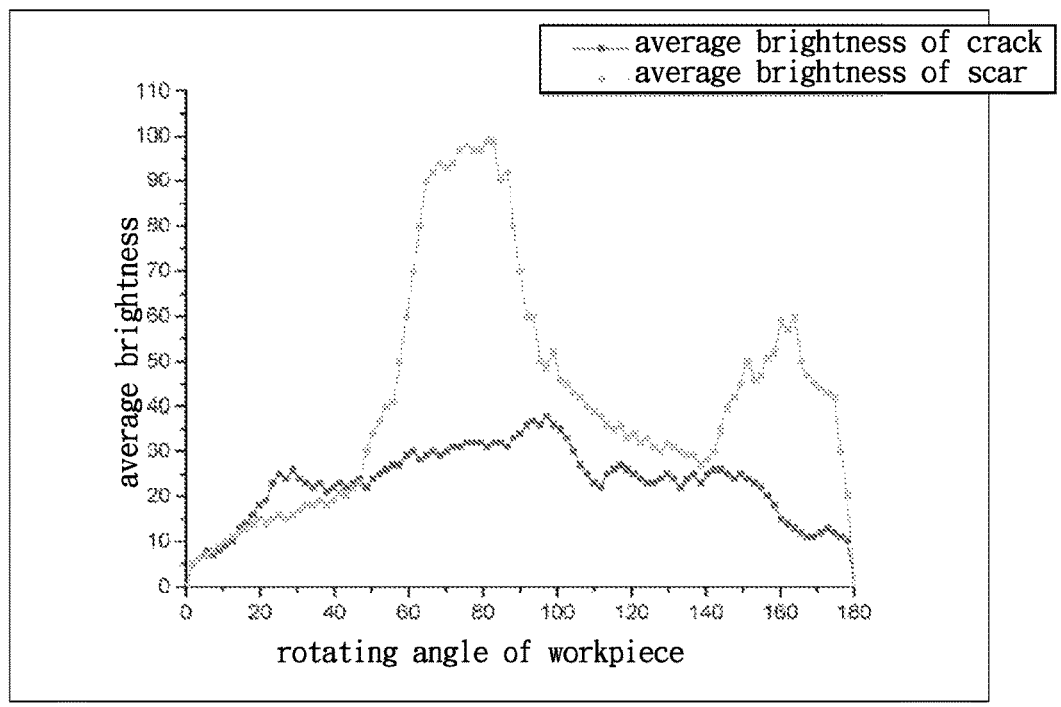
FIG. 12 is a diagram of the industrial visual stethoscope method in FIG. 10, showing the energy received by the camera module.
Figure 13:
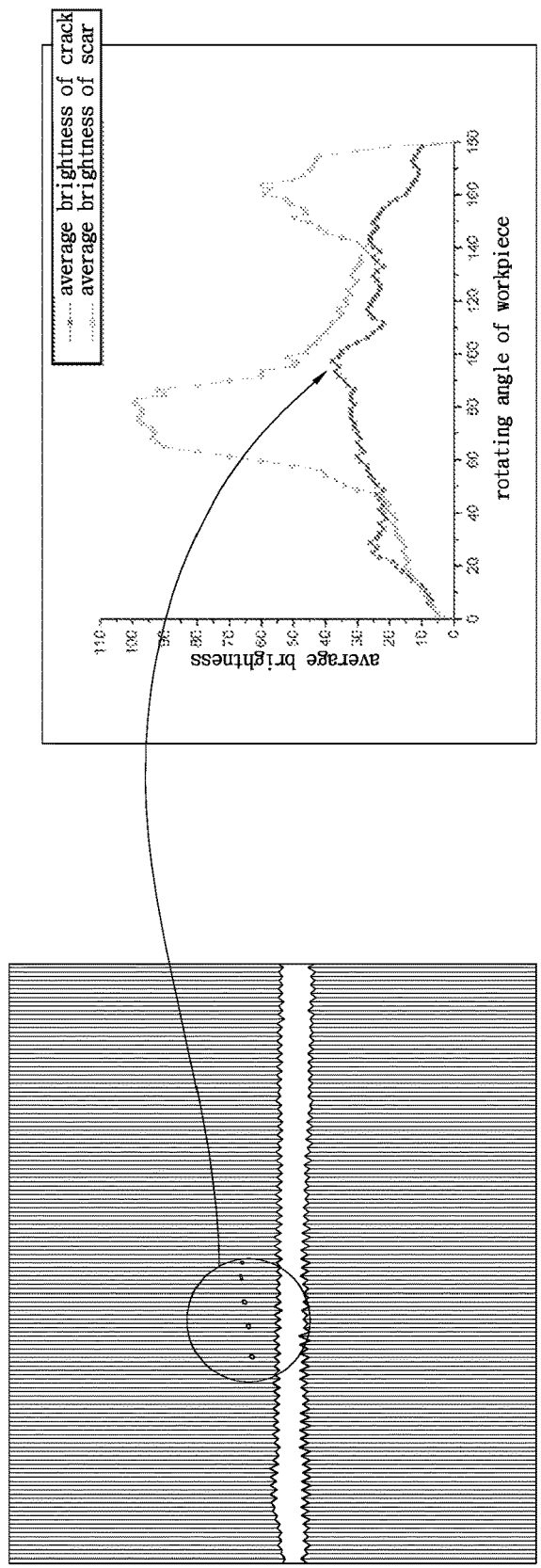
FIG. 13 is a schematic view depicted from a film of the camera module of the industrial visual stethoscope method in FIG. 10, showing the crack without overexposure.
Figure 14:
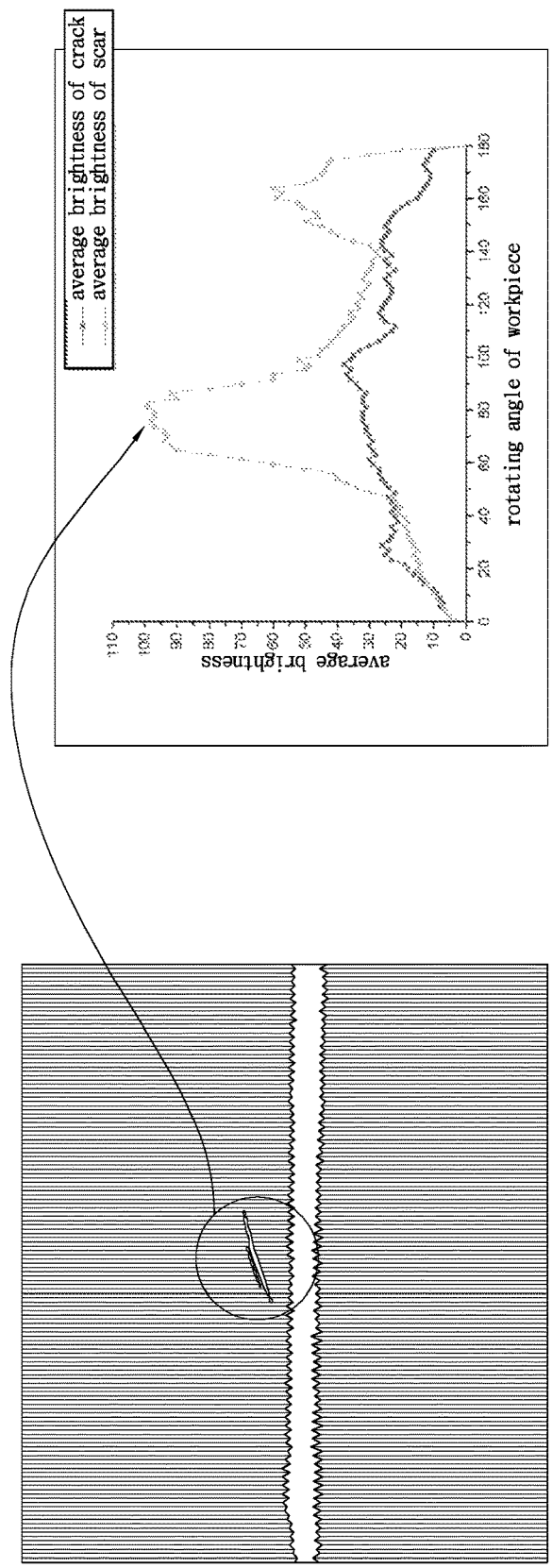
FIG. 14 is a schematic view depicted from the film of the camera module of the industrial visual stethoscope method in FIG. 10, showing the scar that is overexposed.
Figure 15:
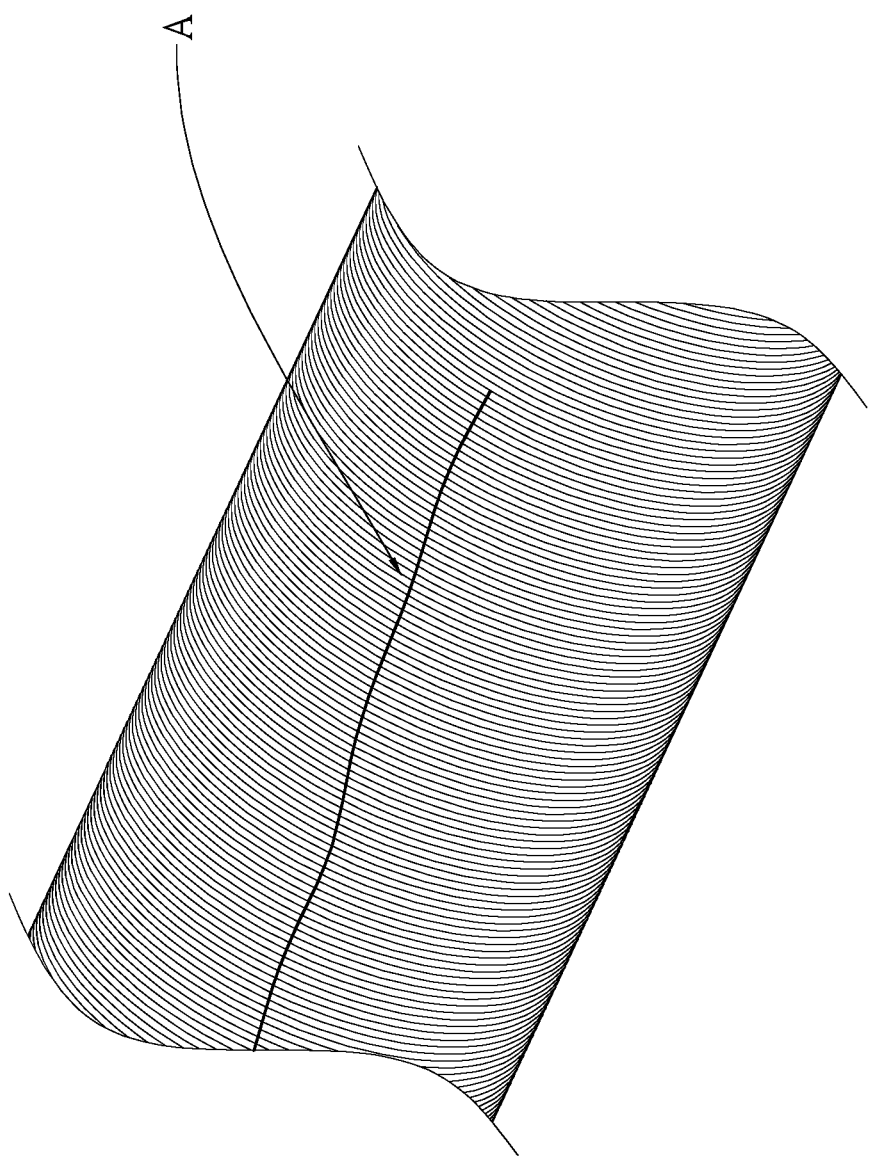
FIG. 15 is a schematic view of the crack on the workpiece of the industrial visual stethoscope method in FIG. 10.
Figure 16:
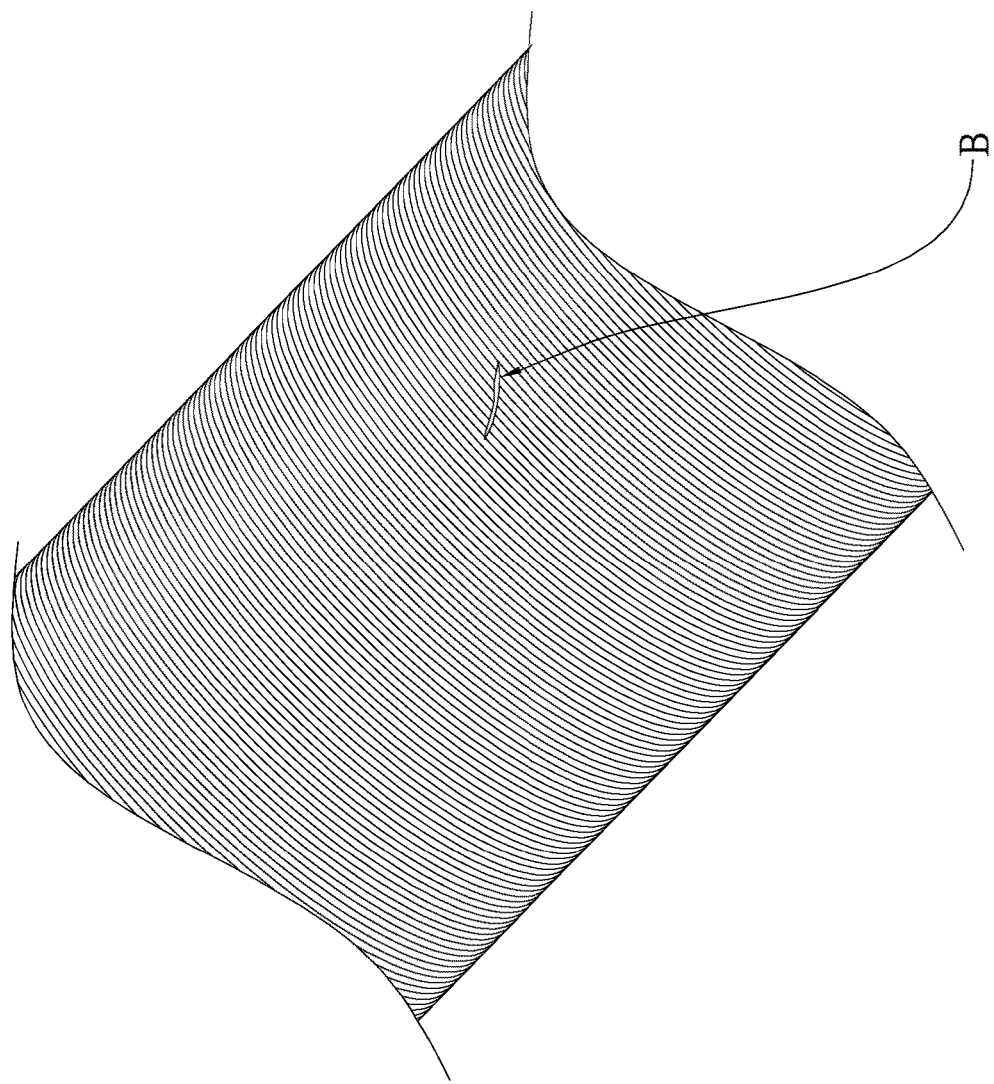
FIG. 16 is a schematic view of the scar on the workpiece of the industrial visual stethoscope method in FIG. 10.
Figure 17:
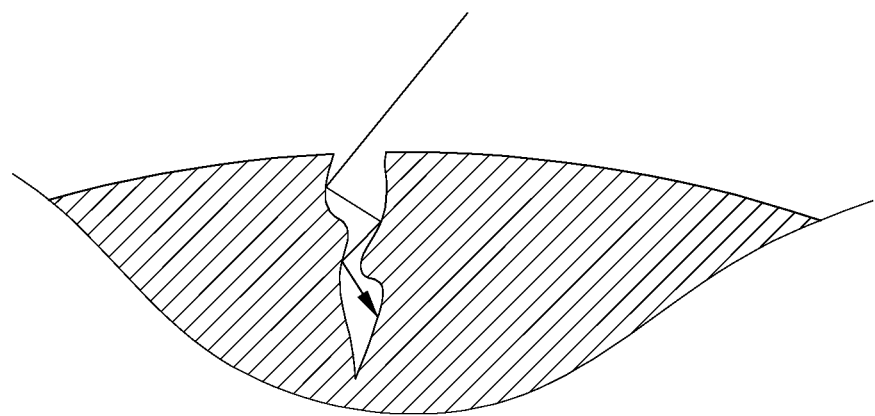
FIG. 17 is a schematic view of the industrial visual stethoscope method in FIG. 10, showing the light enters the crack.
Figure 18:
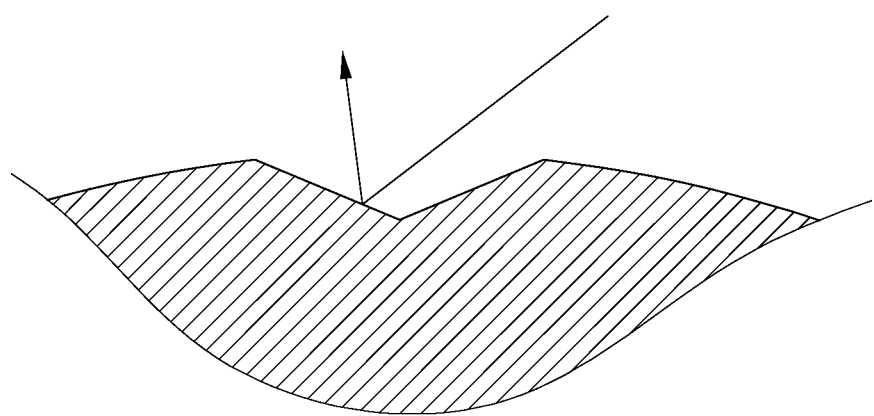
FIG. 18 is a schematic view of the industrial visual stethoscope method in FIG. 10, showing the light enters the scar.

In the second step, when the single-color light device 50 irradiates the workpiece 100, if the single-color light irradiates into the crack which is relatively deep and narrow, the single-color light is rarely to be reflected out of the crack as shown in FIGS. 13 and 17, and thus there is no obvious reflected light. But if the single-color light irradiates into the scar, which is relatively shallow and wide, the single-color light is reflected out of the scar due to the specular reflection (the angle of incidence is equal to the angle of reflection) as shown in FIGS. 14 and 18. During the relative rotation, when the reflected light enters the camera module 70 in parallel, the energy of the light is concentrated since the light enters in the right angle, thereby causing overexposure and forming obvious white light. Therefore, there is an obvious reflected light during the relative rotation, and a RGB value of the high-brightness white light is almost (255,255,255). With reference to FIG. 12, a horizontal axis represents the rotating angle, and the vertical axis represents brightness sensed by the camera module 70. From FIG. 12, when the workpiece 100 is rotated to a specific angle, the energy (brightness) rises greatly to a peak, and then declines. Since the scar formed by hit may form one or multiple reflective surfaces, the amount of the peak in FIG. 12 may be one or multiple.

In addition, whether the overexposure is due to the specular reflection or not may be identified from the brightness, either according to the height or the slope of the brightness. For example, in a preferred embodiment, when the brightness is higher than a threshold value, the light is identified as overexposure. The threshold value in the preferred embodiment may be 50 as shown in FIG. 12. Besides, the specific identifying method also may be learned or improved by Artificial Intelligence from vast quantities of repeated operations.

Besides, a filming range of the camera module 70 is high enough to cover half of the side surface of the workpiece 100, but the rotation angle still reaches 360 degrees, thereby ensuring the camera module 70 can film all the recesses on the workpiece from various angles. However, the rotation angle may be increased or decreased depending on demand.

Moreover, when the workpiece and the group comprising the single-color lighting device 50 and the camera module 70 are relatively rotated, the overall rotating angle (for example, the rotating angle of the workpiece 100) may be obtained or converted from the rotating angle of the abutting wheel 34. Or, the present invention also can comprise another device to detect the overall rotating angle.

The third step (S3) is to distinguish. An analyzing device analyzes a film filmed by the camera module 70. The brightness of all the recesses on the workpiece 100 is altered during the relative rotation, and the analyzing device distinguishes the recess that is overexposed due to specular reflection on the workpiece 100. Then the analyzing device records the result. Afterwards, the analyzing device compares all the recesses on the surface of the workpiece 100 with the recess that is overexposed in the film. If there is any recess overexposed, said overexposed recess is a scar formed by hit. If there is any recess that is not overexposed, said recess not overexposed is a crack. The detecting method is accomplished.

All the recesses on the surface of the workpiece 100 may be recorded in advance, or may be recorded simultaneously by another camera module in the third step (S3), or may be recorded after the recess that is overexposed has been filmed. In addition, all the recesses on the surface of the workpiece 100 may be observed by naked eye or filmed by the camera module 70 automatically.

In the third step (S3), the comparison between all the recesses on the workpiece 100 and the recess that is overexposed may be performed manually or by machine. The machine performing the comparison can achieve the automatic process and can perform all the steps rapidly to raise the efficiency.

The present invention detects whether a large area of specular reflection is incurred via the alternation of an incident angle to make the reflected light enter the camera module 70 in parallel to form overexposure when the camera module 70 is forming images, and thereby the analyzing device can distinguish the scar from the crack.

The present invention detects the scar and the crack only via the single-color lighting device 50 and the camera module 70, such that the present invention will not harm the environment and the human body.

In addition, the single-color lighting device 50 and the camera module 70 may be mounted through a tubular workpiece, thereby detecting an inner wall of the tubular workpiece.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An industrial visual stethoscope system comprising:
   a base;
   a workpiece support mounted on the base for accommodating a workpiece to be detected, and having two first wheel seats and two second wheel seats spaced apart from each other, wherein each of the first wheel seats has a rotating wheel and the two rotating wheels of the two first wheel seats respectively abut two sides of the workpiece, and each of the second wheel seats has a rotating wheel and the two rotating wheels of the two second wheel seats respectively abut another two sides of the workpiece;
   at least one single-color lighting device mounted on the base, and disposed toward the workpiece support;
   at least one camera module mounted on the base, and disposed toward the workpiece support;
   a rotating device mounted on the base to relatively rotate the workpiece on the workpiece support and a group comprising the at least one single-color lighting device and the at least one camera module, the rotating device having:
      a motor mounted on the base; and
      an abutting wheel connected to the motor, rotated by the motor, and abutting the workpiece on the workpiece support; and
   a processor electrically connected to the at least one camera module for analyzing a film filmed by the at least one camera module to detect a recess that is overexposed in the film due to specular reflection on the workpiece.

2. The industrial visual stethoscope system as claimed in claim 1, wherein the workpiece support further has two wheel seat channels; the two first wheel seats are movably mounted on one of the wheel seat channels, and the two second wheel seats are movably mounted on the other wheel seat channel.

3. The industrial visual stethoscope system as claimed in claim 2, wherein the workpiece support further has two base channels; the base channels are perpendicular to the wheel seat channels in extending directions; each of the wheel seat channels is movably mounted across the two base channels.

4. The industrial visual stethoscope system as claimed in claim 1 further comprising a lighting frame mounted on the base; wherein the at least one single-color lighting device is up-and-down movably mounted on the lighting frame, and is up-and-down tiltable relative to the lighting frame.

5. The industrial visual stethoscope system as claimed in claim 1 further comprising a camera frame mounted on the base; wherein the at least one camera module is up-and-down movably mounted on the camera frame, and is up-and-down tiltable relative to the camera frame.

6. The industrial visual stethoscope system as claimed in claim 5, wherein the at least one camera module is transversely moveably mounted on the camera frame.

7. The industrial visual stethoscope system as claimed in claim 1 further comprising an inside frame disposed above the workpiece support for mounting through the workpiece; wherein the at least one single-color lighting device and the at least one camera module are mounted on the inside frame.

8. The industrial visual stethoscope system as claimed in claim 7, wherein the rotating device further has
   a sliding seat mounted on the base; and
   a main frame movably mounted on the sliding seat; the motor and the abutting wheel mounted on the main frame.

9. The industrial visual stethoscope system as claimed in claim 1 further comprising
   a cover mounted on the base, and enclosing the workpiece support, the at least one single-color lighting device, and the at least one camera module; wherein an inner wall of the cover is an unreflecting black wall.

10. An industrial visual stethoscope method comprising the following steps:
   (a) preparing materials, wherein a workpiece, a workpiece stand, a rotating device, a single-color lighting device, and a camera module are prepared, the workpiece are held between multiple rotating wheels of the workpiece stand and an abutting wheel of the rotating device, and the single-color lighting device and the camera module are disposed toward the workpiece;
   (b) filming, wherein the workpiece and a group comprising the single-color lighting device and the camera module are relatively rotated by the rotating wheels of the workpiece stand and the abutting wheel of the rotating device; simultaneously, the single-color lighting device irradiates the workpiece with a single-color light, and the camera module films the workpiece; and
   (c) distinguishing, wherein a processor detects a recess that is overexposed due to specular reflection on the workpiece by a film filmed by the camera module and then the processor records a detected result; afterwards, comparing all the recesses on the workpiece with the recess that is overexposed in the film; if there is any recess that is not overexposed, said recess not overexposed is a crack.

* * * * *